US009861943B2

(12) United States Patent
Vogt et al.

(10) Patent No.: US 9,861,943 B2
(45) Date of Patent: Jan. 9, 2018

(54) VACUUM MIXING SYSTEM AND METHOD FOR THE MIXING OF POLYMETHYLMETHACRYLATE BONE CEMENT

(71) Applicant: Heraeus Medical GmbH, Wehrheim (DE)

(72) Inventors: Sebastian Vogt, Erfurt (DE); Thomas Kluge, Vallendar (DE)

(73) Assignee: Heraeus Medical GmbH, Wehrheim (DE)

( * ) Notice: Subject to any disclaimer, the term of this patent is extended or adjusted under 35 U.S.C. 154(b) by 16 days.

(21) Appl. No.: 15/207,781

(22) Filed: Jul. 12, 2016

(65) Prior Publication Data

US 2017/0014786 A1    Jan. 19, 2017

(30) Foreign Application Priority Data

Jul. 13, 2015    (DE) .................. 10 2015 111 320

(51) Int. Cl.
*B01F 3/12*    (2006.01)
*A61B 17/88*    (2006.01)
(Continued)

(52) U.S. Cl.
CPC ........ *B01F 3/1271* (2013.01); *A61B 17/8827* (2013.01); *A61B 17/8833* (2013.01); *A61L 24/06* (2013.01); *B01F 3/14* (2013.01); *B01F 11/0054* (2013.01); *B01F 13/003* (2013.01); *B01F 13/0023* (2013.01); *B01F 13/06* (2013.01); *B01F 15/00506* (2013.01); *B01F 15/0206* (2013.01); *B01F 15/0237* (2013.01);
(Continued)

(58) Field of Classification Search
None
See application file for complete search history.

(56) References Cited

U.S. PATENT DOCUMENTS 4,671,263 A * 6/1987 Draenert ............ A61B 17/8802
366/139
4,758,096 A * 7/1988 Gunnarsson ............ B01F 13/06
366/139
(Continued)

FOREIGN PATENT DOCUMENTS

DE        3 640 279 A1    6/1987
DE        69812726 T2    2/2004
(Continued)

*Primary Examiner* — Peter A Salamon
(74) *Attorney, Agent, or Firm* — Norris McLaughlin & Marcus, P.A.

(57) ABSTRACT

Vacuum mixing systems and methods mix of polymethylmethacrylate bone cement, the systems and methods comprise at least one cartridge having an evacuable internal space, a pump with a plunger that can be moved by hand to generate a low pressure, and a connecting conduit connecting the internal space of the at least one cartridge to the pump. The pump comprises an operating element that can be operated from outside and is connected appropriately to the plunger such that it is suitable for moving the plunger in the pump by hand such that a low pressure can be generated such that the low pressure of the pump can be used to evacuate gas from the internal space of the at least one cartridge through the connecting conduit.

17 Claims, 7 Drawing Sheets

(51) Int. Cl.
  *B01F 11/00* (2006.01)
  *B01F 13/00* (2006.01)
  *B01F 13/06* (2006.01)
  *B01F 15/02* (2006.01)
  *A61L 24/06* (2006.01)
  *B01F 3/14* (2006.01)
  *B01F 15/00* (2006.01)

(52) U.S. Cl.
  CPC ...... *B01F 15/0258* (2013.01); *B01F 15/0278* (2013.01); *B01F 15/0279* (2013.01); *A61B 2017/8838* (2013.01); *A61L 2430/02* (2013.01); *B01F 2003/1257* (2013.01); *B01F 2215/0029* (2013.01)

(56) References Cited

U.S. PATENT DOCUMENTS

| | | | | |
|---|---|---|---|---|
| 4,973,168 A * | 11/1990 | Chan | ............... | A61B 17/8805 206/219 |
| 5,100,241 A | 3/1992 | Chan | | |
| 5,344,232 A * | 9/1994 | Nelson | ............... | A61B 17/8822 141/23 |
| 5,551,778 A * | 9/1996 | Hauke | ............... | B01F 11/0082 206/222 |
| 5,586,821 A * | 12/1996 | Bonitati | ............... | A61B 17/8825 366/139 |
| 5,588,748 A * | 12/1996 | Nomura | ............... | G01J 5/02 374/158 |
| 5,624,184 A | 4/1997 | Chan | | |
| 5,997,544 A * | 12/1999 | Nies | ............... | A61B 17/8802 606/92 |
| 6,033,105 A * | 3/2000 | Barker | ............... | A61B 17/8816 222/241 |
| 6,709,149 B1 * | 3/2004 | Tepic | ............... | A61L 24/06 366/139 |
| 7,073,936 B1 * | 7/2006 | Jonsson | ............... | B01F 11/0082 366/139 |
| 8,662,736 B2 * | 3/2014 | Vogt | ............... | A61B 17/8833 366/139 |
| 8,757,866 B2 * | 6/2014 | Vogt | ............... | A61B 17/8825 222/190 |
| 2010/0329074 A1 * | 12/2010 | Vogt | ............... | A61B 17/8825 366/190 |
| 2011/0184083 A1 * | 7/2011 | Vogt | ............... | B01F 7/00291 523/116 |
| 2012/0006874 A1 * | 1/2012 | Vogt | ............... | B67B 7/92 225/103 |
| 2012/0026825 A1 * | 2/2012 | Vogt | ............... | A61B 17/8833 366/176.3 |
| 2012/0132675 A1 * | 5/2012 | Vogt | ............... | A61B 17/8825 222/327 |
| 2013/0135957 A1 * | 5/2013 | Vogt | ............... | B29B 7/12 366/75 |
| 2013/0135959 A1 * | 5/2013 | Vogt | ............... | B29B 7/28 366/139 |
| 2013/0182528 A1 * | 7/2013 | Vogt | ............... | A61B 17/8822 366/75 |

FOREIGN PATENT DOCUMENTS

| | | |
|---|---|---|
| DE | 10 2009 031 178 B3 | 9/2010 |
| EP | 0 692 229 A1 | 1/1996 |
| EP | 0796653 A2 | 9/1997 |
| EP | 1 005 901 A2 | 6/2000 |
| EP | 1 016 452 A2 | 7/2000 |
| EP | 1 020 167 A2 | 7/2000 |
| EP | 1886647 A1 | 2/2008 |
| WO | 94 26403 A1 | 11/1994 |
| WO | 99 67015 A1 | 12/1999 |

* cited by examiner

VACUUM MIXING SYSTEM AND METHOD FOR THE MIXING OF POLYMETHYLMETHACRYLATE BONE CEMENT

This application claims foreign priority benefit under 35 U.S.C. 119 of German Application No. DE 10 2015 111 320.1 filed Jul. 13, 2015.

The invention relates to a vacuum mixing system for the mixing of polymethylmethacrylate bone cement (PMMA bone cement) from two starting components, in particular for the mixing of a medical bone cement, and for storage of the starting components. The invention further relates to a method for the mixing of polymethylmethacrylate bone cement.

Accordingly, the subject matter of the invention is a vacuum mixing system for the storage, mixing, and, if applicable, dispensing of polymethylmethacrylate bone cement. The invention further relates to a method for the transferring of monomer liquid into the vacuum mixing system and to a method for the mixing of the components of polymethylmethacrylate bone cement.

Polymethylmethacrylate bone cements (PMMA bone cements) are based on the pioneering work of Sir Charnley. PMMA bone cements consist of a liquid monomer component and a powder component. The monomer component generally contains the monomer, methylmethacrylate, and an activator (N,N-dimethyl-p-toluidine) dissolved therein. The powder component, which is also referred to as bone cement powder, comprises one or more polymers, a radiopaquer, and the initiator dibenzoylperoxide. The polymers of the powder component are produced on the basis of methylmethacrylate and comonomers, such as styrene, methylacrylate or similar monomers by means of polymerisation, preferably by suspension polymerisation. During the mixing of powder component and monomer component, swelling of the polymers of the powder component in the methylmethacrylate generates a dough that can be shaped plastically and is the actual bone cement. During the mixing of powder component and monomer component, the activator, N,N-dimethyl-p-toluidine, reacts with dibenzoylperoxide while forming radicals. The radicals thus formed trigger the radical polymerisation of the methylmethacrylate. Upon advancing polymerisation of the methylmethacrylate, the viscosity of the cement dough increases until the cement dough solidifies.

Methylmethacrylate is the monomer used most commonly in polymethylmethacrylate bone cements. Redox initiator systems usually consist of peroxides, accelerators and, if applicable, suitable reducing agents. Radicals are formed only if all ingredients of the redox initiator systems act in concert. For this reason, the ingredients of the redox initiator system in the separate starting components are arranged appropriately such that these cannot trigger a radical polymerisation. The starting components are stable during storage provided their composition is adequate. Only when the two starting components are mixed to produce a cement dough, the ingredients of the redox initiator system, previously stored separately in the two pastes, liquids or powders react with each other forming radicals which trigger the radical polymerisation of the at least one monomer. The radical polymerisation then leads to the formation of polymers while consuming the monomer, whereby the cement dough is cured.

PMMA bone cements can be mixed by mixing the cement powder and the monomer liquid in suitable mixing beakers with the aid of spatulas. One disadvantage of said procedure is that air inclusions may be present in the cement dough thus formed and can cause destabilisation of the bone cement later on. For this reason, it is preferred to mix bone cement powder and monomer liquid in vacuum mixing systems, since mixing in a vacuum removes air inclusions from the cement dough to a large extent and thus achieves optimal cement quality. Bone cements mixed in a vacuum have clearly reduced porosity and thus show improved mechanical properties. A large number of vacuum cementing systems have been disclosed of which the following shall be listed for exemplary purposes: U.S. Pat. No. 6,033,105 A, U.S. Pat. No. 5,624,184 A, U.S. Pat. No. 4,671,263 A, U.S. Pat. No. 4,973,168 A, U.S. Pat. No. 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, U.S. Pat. No. 5,344,232 A. In the vacuum cementing systems thus specified, there is a need to connect an external vacuum pump to generate the low pressure. These are generally operated by compressed air utilising the Venturi principle. The compressed air required for operation of the vacuum pumps is supplied either by stationary compressed air facilities or by electrically-operated compressors. In addition, it is also feasible to use electrically-operated vacuum pumps to generate vacuum.

Cementing systems, in which both the cement powder and the monomer liquid are already packed in separate compartments of the mixing systems and are mixed with each other in the cementing system only right before application of the cement, are a development of cementing technology. Said full-prepacked mixing systems were proposed through EP 0 692 229 A1, DE 10 2009 031 178 B3, U.S. Pat. No. 5,997,544 A, U.S. Pat. No. 6,709,149 B1, DE 698 12 726 T2, and U.S. Pat. No. 5,588,745 A. Said mixing systems also require an external vacuum source. In this context, the DE 10 2009 031 178 B3 patent discloses a vacuum mixing device having a two-part dispensing plunger that can also be used for a vacuum mixing device according to the invention.

If vacuum mixing systems are used for cementing, external vacuum pumps need to be provided. Said vacuum pumps are expensive and need to be cleaned after use. Moreover, vacuum hoses for connecting the vacuum pumps to the vacuum mixing systems are required. Said vacuum hoses need to be enclosed with the vacuum mixing systems. Accordingly, prior to the mixing using a vacuum mixing system, the vacuum pump first needs to be set-up in the surgical theatre (OR) and must be connected to an energy source, such as compressed air or electrical power. Then, the vacuum pump is connected to the vacuum mixing system by means of a vacuum hose. Said installation steps take up costly OR time and are potentially error-prone. The vacuum pump and connecting conduits to the vacuum mixing system and to external energy sources and supply conduits take up space and are potential tripping hazards and stumbling blocks that can disturb the often hectic procedure during a surgery.

EP 0 796 653 A2 discloses a system for mixing bone cement, in which a manually operated pump and a monomer liquid container are connected on top of a cartridge containing cement powder. A disadvantage is that the system must first be assembled and mounted, and thereby the operation is complicated. In addition, the monomer liquid can penetrate before evacuating the interior of the cartridge into the cartridge, where it reacts prematurely with the cement powder. This may cause unbalanced bone cement. In addition, the monomer must seep through the cement powder to achieve complete mixing or the contents must be thoroughly mixed. Further, the low-lying areas in the cement powder cannot easily be evacuated, whereby unwanted air pockets can result in the mixed bone cement dough.

An interesting concept has been proposed through EP 1 886 647 A1. Here, the cement powder is stored in an evacuated cartridge and the monomer liquid is situated in a separate container. The cartridge, which is kept at a low pressure, being opened causes the monomer liquid to be aspirated into the cartridge without any ingress of air. A bone cement dough free of air inclusions is thus produced. Said concept requires the cartridge to remain closed in vacuum-tight manner during the storage before use such that no non-sterile air can enter into the cartridge. For this purpose, the cartridge must be hermetically sealed in a stable manner. Accordingly, one associated disadvantage is that the design is quite elaborate and that the content of the cartridge cannot be mixed by an externally-operated mixing system after aspiration of the monomer since a feed-through for a mixing rod or for a mixing tube would not readily be permanently vacuum-tight.

Accordingly, it is the object of the invention to overcome the disadvantages of the prior art. In particular, the disadvantages of the known vacuum mixing systems with an external vacuum source shall be overcome without having to maintain a low pressure for a long period of time. It is the object of the invention, specifically, to develop a vacuum mixing system, in which a low pressure is generated only just before the cement components are being mixed. The device is to be as simple as possible and shall allow a low pressure with respect to the surrounding atmosphere to be generated, at least once, in a cement cartridge. Moreover, it can be advantageous that the vacuum mixing system is capable of enabling a transfer of monomer liquid from a monomer container into a cartridge filled with cement powder. Moreover, a method is then to be provided that enables a monomer transfer and a vacuum mixing in full-prepacked mixing systems. Moreover, the vacuum mixing system to be developed shall be manufactured mainly from inexpensive plastics.

It is an object of the invention to develop a simple closed device, in which polymethylmethacrylate bone cement powder and monomer liquid can be stored in separate compartments and can be mixed with each other subsequently. A medical user shall be enabled to combine and mix the polymethylmethacrylate bone cement powder and the monomer liquid inside the device, without the medical user being exposed to both cement components. Exposure of the medical user to the polymethylmethacrylate bone cement powder and to the monomer liquid must be excluded. The device to be developed is a full-prepacked mixing system. The device shall be designed appropriately such that a transfer of the monomer liquid into the polymethylmethacrylate bone cement powder takes place by means of a vacuum without the use of external vacuum pumps. Moreover, the device shall ensure the production of bone cement dough functionally and reliably without the use of external energy sources, such as compressed air, vacuum or electrical current, even under the simplest external conditions. Particularly preferably, the device shall also be largely independent of an internal energy store, such as, for example, batteries or mechanical energy stores. The device is to be usable autonomously without any additional technical equipment.

Moreover, a device that is inexpensive to manufacture and working reliably for the mixing of a medical cement and, if applicable, for storage of the starting components, and a method for the mixing of the bone cement is to be devised, in which a simple manual operation can be used to mix the starting components, if possible without air inclusions arising in the mixing material.

The main component of the polymethylmethacrylate bone cement, as mixing material, shall be a powder and the second component shall be present in the form of a liquid. Preferably, it shall be possible to store the two starting components of the bone cement separate from each other in the vacuum mixing system and to combine them safely through the use of the device.

The objects of the invention are met by a vacuum mixing system for the mixing of polymethylmethacrylate bone cement, comprising at least one cartridge having an evacuable internal space for mixing of the bone cement, a pump with a plunger that can be moved by hand to generate a low pressure, and a connecting conduit connecting the internal space of the at least one cartridge to the pump for generating a low pressure, whereby the pump comprises an operating element that can be operated from outside and is connected appropriately to the plunger such that it is suitable for moving the plunger in the pump by hand such that a low pressure can be generated such that the low pressure of the pump can be used to evacuate gas from the internal space of the at least one cartridge through the connecting conduit, whereby a cement powder is contained in the cartridge and the vacuum mixing system comprising a container separate from the cartridge, the container containing a monomer liquid, whereby the container is connected via a liquid line to the cartridge, whereby the liquid conduit opens at the front side of the cartridge into the cartridge, and the connection conduit opens on the opposite rear side of the cartridge into the cartridge.

The front side of the cartridge is arranged under normal operation of the vacuum mixing system downward and the rear side upward accordingly. Thereby, the cement powder is lying inside down on the front side of the cartridge and the monomer liquid is drawn with the low pressure from below through the cement powder in the direction of the connection conduit to the top. In this way, good mixing of the cement powder with the monomer liquid is achieved and it is simultaneously ensured that the mixture of the cement powder with the monomer liquid is carried out under a reduced pressure, so that the danger of air inclusions inside the bone cement dough is reduced.

Theoretically, multiple movable plungers could be provided just as well of which at least one can be moved by hand. In the scope of the present invention, the plunger that can be moved by hand is at least one of the multiple movable plungers.

In the scope of the present invention, a plunger that can be moved by hand can just as well be implemented by a side wall that can be moved by hand. What is important is that the plunger driven by hand increases the volume in the pump appropriately such that a low pressure arises in the pump that can be used for pumping.

Preferably, the invention can provide the plunger to be shiftable by hand axially in a hollow cylinder in the pump.

Presently, low pressure shall be understood to mean a pressure related to the ambient atmosphere that is less than the ambient atmospheric pressure.

Preferably, the pump can be provided to be integrated into the vacuum mixing system.

Preferably, the polymethylmethacrylate bone cement is mixed and/or can be produced from at least two components. Thereby one component is the monomer liquid and the other component is the cement powder.

Preferably, the invention can provide the pressure in the internal space of the at least one cartridge to be reducible by at least 50%, preferably to be reducible by at least 90%, by the pumping process.

According to the invention, the starting components for the mixing material, in particular for the PMMA bone cement, are already present in the cartridges.

It is preferred, according to the invention, that the device is also well-suited for storage of the starting components, in particular when the containers are inserted into the device or the containers are a fixed part of the device.

The mixing material is particularly preferred to be a bone cement, in particular a PMMA bone cement.

A refinement of the invention can just as well provide that gas can be evacuated through the connecting conduit from the internal space of the at least one cartridge by the low pressure and that gas can be evacuated from a conduit between the internal space of the cartridge and the container by the low pressure and that the monomer liquid to be mixed with the cement powder of the PMMA bone cement in the cartridge can be drawn from the container into the internal space of the cartridge by the low pressure.

Vacuum mixing systems according to the invention can be provided appropriately such that the pump comprises a gas-tight pumping space on the inside and has the mobile plunger limiting the pumping space arranged in it, whereby the plunger can be driven by hand in a direction, preferably unidirectionally, such that the motion of the plunger enlarges the pumping space and the low pressure thus arising in the pumping space allows the internal space of the at least one cartridge to be evacuated through the connecting conduit.

Due to the specific requirements, such as the volume of the internal space of the cartridge being small, there is no need to have more elaborate pump systems present.

In this context, the invention can provide the volume enlargement of the pumping space to be at least equal to the free volume of the internal space of the cartridge, preferably the volume enlargement of the pumping space to be at least equal to the sum of the volume of the internal space of the cartridge and the volume of the connecting conduit and the volume of a conduit between the internal space and the liquid container and the volume of the monomer liquid in the liquid container to be mixed in the cartridge with the cement powder.

This ensures that the pump can evacuate the internal space of the cartridge. In this context, the volume of the pumping space prior to the pumping process is as small as possible in an ideal case. Accordingly, the invention can preferably provide the volume of the pumping space after the pumping process to be at least 10 times larger than the volume of the pumping space before the pumping process, particularly preferably to be at least 20 times larger than the volume of the pumping space before the pumping process. Preferably, the plunger does not touch flush against the internal space of the pump, in particular the cover surface of a hollow cylinder with the connector for the connecting conduit, such that the plunger does not get suctioned against said surface and is therefore difficult to move for starting the motion.

The cement powder is the first (powdery) component of the PMMA bone cement and the monomer liquid is the second component of the PMMA bone cement.

Moreover, the invention can provide the vacuum mixing system to comprise a mixing device for the mixing of the content of the at least one cartridge, whereby the mixing device is preferred to be arranged in the internal space of the cartridge and can be driven by hand or through a motor.

Preferably, the cartridge comprises a pressure-tight feed-through through which a rod or a mixing tube is guided by means of which the mixing device can be operated from outside the cartridge. For this purpose, the rod or the mixing tube is preferred to be mounted appropriately in the feed-through such that it can rotate and be shifted in longitudinal direction. The mixing device can be used to mix the cartridge content well.

Preferred embodiments can be characterized in that the total weight of the vacuum mixing system is less than 30 kg, particularly preferably the total weight is less than 10 kg.

The design, according to the invention, of the mixing device having an operating element that can be operated by hand and having the pump enables the weights to be as low as specified. The weight being low is advantageous in that the mixing device can be taken along and can be used without any connection to supply conduits and without major preparation in advance.

Moreover, the invention can provide the plunger to be supported in a hollow cylinder such as to be axially mobile, whereby the hollow cylinder is closed on a first side or is closed except for one feed-through for a rod connected to the operating element and the plunger, in particular is closed by a closure, and the hollow cylinder is open on a second side, whereby a pumping space is preferably formed in the hollow cylinder between the plunger and the first closed side.

By this means, i.e. the cylindrical geometry, a pump is proposed that is particularly easy and inexpensive to fabricate and easy to operate and particularly non-susceptible to malfunction.

The invention can just as well provide the plunger to be connected to the operating element by means of a rod and, preferably, the plunger to be movable in the pump by pushing the operating element.

By this means, a particularly simple vacuum mixing system is provided that is not associated with a major risk of malfunction. The direct connection of the operating element to the plunger by means of the rod can be implemented in the form of a one-part injection moulded part made of plastics. Alternatively, a transmission and/or a gear can be provided by means of which the force exerted on the operating element is transmitted to the plunger to enable a more forceful motion of the plunger.

Moreover, the a refinement provides a mobile dispensing plunger for dispensing the mixed bone cement from the cartridge to be arranged in the internal space of the cartridge, whereby the dispensing plunger preferably is or can be locked in place in detachable manner in order to prevent the dispensing plunger from moving in response to the effect of the low pressure.

The dispensing plunger simplifies the operation of the vacuum mixing system.

In this context, the invention can provide the dispensing plunger to comprise a passage with a gas-permeable pore disk that is impermeable for the cement powder, whereby the passage with the pore disk connects the internal space of the cartridge to the surroundings in gas-permeable manner, whereby the passage can be closed in gas-tight manner, preferably can be closed in gas-tight manner by means of a sealing plunger of the dispensing plunger.

Having the pore disk can ensure that the internal space of the cartridge containing the bone cement powder can be sterilised by means of a gas such as ethylene oxide without there being at risk of the bone cement powder leaking out from the internal space of the cartridge into the surroundings.

Moreover, the invention can just as well provide the dispensing plunger to contain a feed-through, in which is situated a mixing rod that can be actuated by hand from outside, whereby a mixing device, in particular one comprising multiple mixing vanes, is attached to the mixing rod in the internal space of the cartridge and allows the content of the internal space of the cartridge to be mixed.

By this means, the content of the cartridge can be mixed easily by hand.

Preferably, the dispensing plunger is arranged on the rear side of the cartridge.

A refinement proposes the cartridge to be a cement cartridge filled with the cement powder, whereby the container is preferably connected, in liquid-impermeable manner, to the internal space of the cement cartridge through a separating element that can be opened, and/or the internal space of the cement cartridge is or can be connected to the pump in gas-permeable manner.

As a result, the monomer liquid from the separate container can be transferred into the internal space of the cartridge by the same pumping motion and/or the same pumping process that is used to evacuate the internal space of the cartridge. In the process, the vacuum and/or the low pressure generated by hand by means of the pump is concurrently used to aspirate the monomer liquid into the cartridge.

The invention can provide the cartridge, the pump, the separate container, and all connecting conduits to be connected to a common foot part either affixed and/or in detachable manner, whereby it is preferred to have the pump, the separate container, and all connecting conduits affixed to the foot part and the cartridge be connected to the foot part in detachable manner.

A vacuum mixing system of this type is easy to set up and operate. This simplifies the application of the vacuum mixing system. There only needs to be a level support at the site of application for set-up of the vacuum mixing system, which would not be a problem in most surgical areas.

Moreover, the invention can provide the liquid conduit between the separate container and the internal space of the cartridge comprising an upward facing loop, whereby the apex of the loop is situated above a junction under a monomer container that is arranged in the separate container.

Accordingly, if the vacuum mixing system is set up correctly, it can be ensured that the monomer liquid cannot inadvertently flow into the cartridge and inadvertently become cured therein without the action of the low pressure. As a result, the monomer liquid in the container can be prevented from already reaching the internal space of the cartridge through the liquid conduit when it is being filled into the separate container and/or when the monomer container (the monomer glass ampoule) is being opened. The effect of the liquid conduit having said U-shaped loop is that the monomer liquid remains in the container up to the level of the apex before the pumping plunger is moved in the direction of the liquid conduit, which prevents premature ingress of the monomer liquid to the cement powder. In particular in the case of high viscosity cements, premature contact even of small volumes of monomer liquid with the cement powder can block, like a glue, the liquid conduit or a conduit means provided as a nozzle, as is described in U.S. Pat. No. 8,662,736 B2. The liquid conduit can be transparent or translucent to allow the user to visually check the monomer transfer. For this purpose, in particular, an inspection window, through which the loop with the highest apex can be seen, can be provided in the device.

A vacuum mixing system according to the invention can be characterised in that the pump is designed to consist of a hollow cylinder, whereby the hollow cylinder is or can be connected to the internal space of the cartridge, a gas-tight closure on one end of the hollow cylinder, a plunger that is arranged such as to be gas-tight and axially mobile in the hollow cylinder, at least one operating element that can be operated by hand and can be used to move the plunger in the pump by hand, whereby the plunger can be moved axially in opposite direction with respect to the closure when the plunger is moved by the at least one operating element that can be operated by hand and thus evacuates gas from the internal space of the cartridge.

Said design is particularly simple and the parts for it can be manufactured from plastics by injection moulding.

Moreover, the invention can provide the plunger to be shifted appropriately after a full stroke of the plunger in the hollow cylinder such that the volume formed by the hollow cylinder, the closure, and the plunger is at least equal to the volume of the internal space of the cartridge to be evacuated.

The effect of matching the volumes is that the pump is dimensioned to be sufficient for the specified purpose.

The underlying objects of the present invention are also met by a method for the mixing of polymethylmethacrylate bone cement in an internal space of a cartridge of a vacuum mixing system, in particular of a vacuum mixing system according to the invention, in which a motion of a manually driven plunger of a pump of the vacuum mixing system is used to generate a low pressure in the pump, whereby the pump thus driven is used to evacuate the internal space of the cartridge from above, whereby a cement powder is contained in the internal space of the cartridge and a gas is evacuated from the internal space of the cartridge by the pump, whereby a monomer liquid is introduced into the internal space of the cartridge from below by the low pressure and then the monomer liquid and the cement powder is mixed in the evacuated internal space of the cartridge to form a bone cement.

Preferably, only a single stroke of the plunger of the pump takes place to generate the low pressure with the pump. Once the bone cement is mixed, the mixed bone cement dough can be extruded from the cartridge with a dispensing plunger. Preferably, the cartridge is first separated from the pump.

Methods according to the invention can provide the volume of a pumping space of the pump to become enlarged by the manual motion of the plunger, and the internal space of the cartridge to be evacuated by the low pressure thus generated.

Moreover, the invention can provide the monomer liquid being aspirated into the internal space of the cartridge by the low pressure in the pump, whereby preferably the monomer liquid is pulled from below through the cement powder.

Moreover, the invention can provide the plunger of the pump to be moved by hand, whereby a low pressure with respect to the ambient atmosphere is generated in the pump, whereby gas is aspirated from the internal space of the cartridge from above through a connecting conduit into the hollow cylinder and the monomer liquid is aspirated from below into the cartridge and into the cement powder, followed by the cement powder being mixed, manually or motor-driven, with the monomer liquid by means of a mixing device, followed by the cartridge with the mixed cement dough being removed and the cement dough being extruded from the cartridge by moving a dispensing plunger axially.

Moreover, the invention can provide the monomer liquid to be arranged in a container that is separate from the cartridge, whereby the monomer liquid is contained in a glass ampoule, the glass ampoule is opened before the plunger is driven by hand such that a liquid-permeable connection is established between the internal space of the cartridge and the container, followed by the plunger being moved axially in the hollow cylinder, whereby a low pressure with respect to the ambient atmosphere is generated, whereby gas is aspirated from the internal space of the cartridge through the connecting conduit into the hollow cylinder, and monomer liquid is aspirated into the cartridge through the low pressure formed in the internal space of the cartridge.

The invention is based on finding, surprisingly, that having a pump that can be driven by hand allows to provide a vacuum mixing system that is independent of internal and external energy sources and other supply conduits. The vacuum mixing system according to the invention can be designed to be compact, lightweight, and space-saving. The pump can be designed to include the easiest means such that the entire vacuum mixing system can be used as a single-use system. Moreover, the pump is used to transfer a monomer liquid into the cement powder. The two components of the PMMA bone cement can then be mixed in a vacuum and/or at the low pressure. By the arrangement of the connecting conduit relative to the pump and the liquid line relative to the container according to the invention it can be ensured, that the bone cement dough can be mixed bubble-free and homogenous under low pressure.

It is another advantage of the vacuum mixing system according to the invention that the gases evacuated from the cartridge are not released to the surroundings since there is then no need to filter these gases in order to remove undesired ingredients (such as, for example, methylmethacrylate vapours). Instead, the gases simply remain inside the pump and/or in the pumping space.

Cementing systems according to the present invention contain a device for generating a vacuum and/or for generating a low pressure that is suitable for temporary generation of a low pressure before and during the mixing of a powdered component with a liquid monomer component of the polymethylmethacrylate bone cement.

The underlying rationale of the invention is based on finding that only a relatively small amount of energy is required, and thus a low manual force needs to be exerted, to generate the vacuum and/or the low pressure in a cartridge required for mixing the starting components of a bone cement at said low pressure or vacuum. The amount of energy required to transfer the monomer liquid into the cement powder is also small. Said small amount of energy can easily be applied by pushing-in a plunger in the pump. As a result, the vacuum mixing system is easy to handle and operate and is independent of internal and external energy stores.

The rationale of the invention is also based on a low pressure being generated in the hollow cylinder of the pump by manually actuating an operating element by means of a connected plunger in a hollow cylinder of the pump, whereby the low pressure is distributed throughout the cartridge by means of a conducting means, and the monomer liquid is aspirated from an opened monomer liquid container into the cartridge containing cement powder. Then, manual mixing of the cement components by means of a mixing rod and a stirring device attached to it takes place.

The manually actuated monomer transfer according to the invention effected by the action of a low pressure can be implemented inexpensively using simple plastic parts that can be produced by injection moulding of plastics. The particular advantage of the device according to the invention is that the device can be operated without requiring external aids, such as compressed air-driven vacuum pumps and vacuum hoses, and without requiring energy sources, such as compressed air or batteries. The device according to the invention can be used autonomously and even under the simplest surgery conditions. The device according to the invention provides a closed full-prepacked mixing system cementing system for price-sensitive markets.

BRIEF DESCRIPTION OF THE DRAWINGS

Further exemplary embodiments of the invention shall be illustrated in the following on the basis of seven schematic figures, though without limiting the scope of the invention. In the figures.

DETAILED DESCRIPTION OF THE DISCLOSURE

Figure 7:
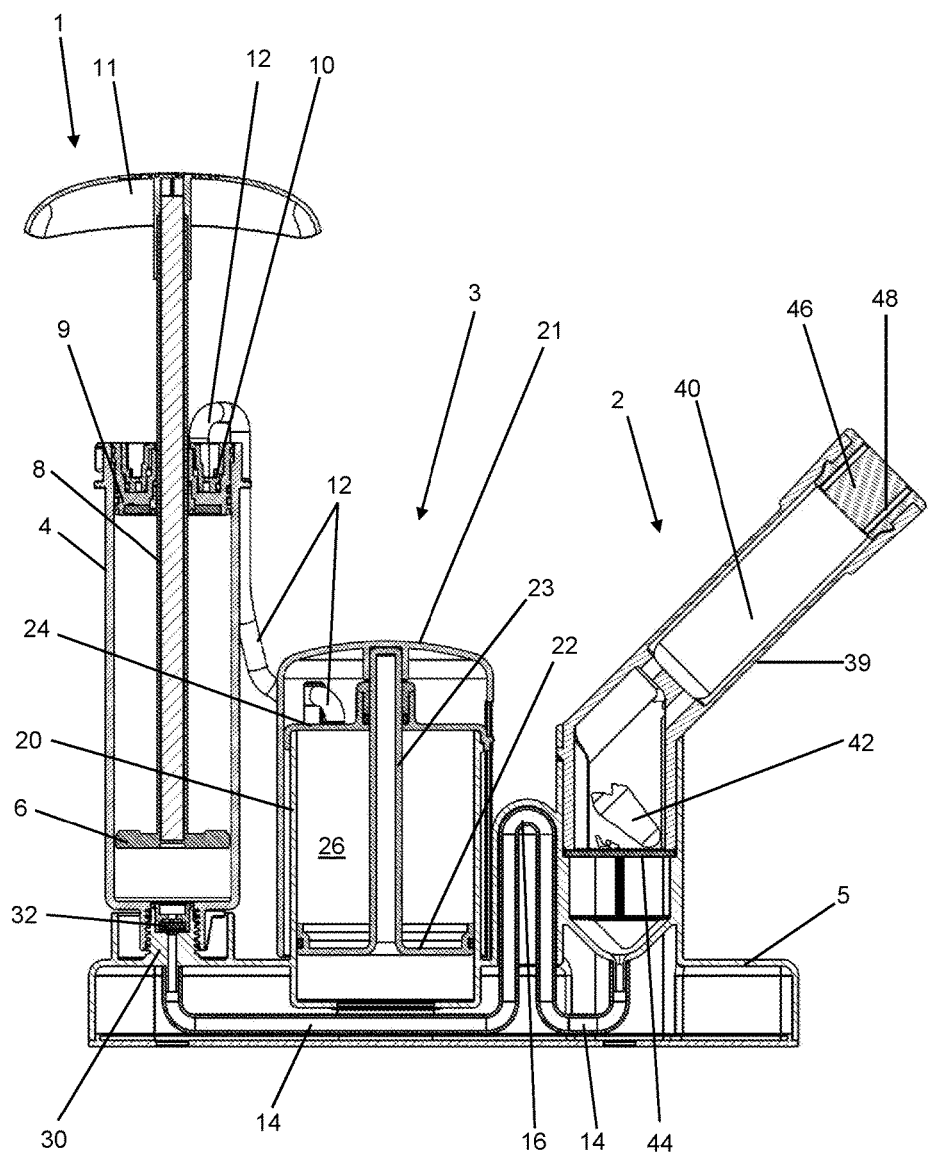
FIG. 7: shows a schematic cross-sectional view of the vacuum mixing system according to FIGS. 1 to 6 sectioned along A-A according to FIG. 2 after the pumping process.

FIGS. 1 to 6 show a various views of a vacuum mixing system according to the invention prior to the pumping process. FIG. 7 shows a schematic cross-sectional view of the vacuum mixing system after the pumping process. The vacuum mixing system essentially consists of three parts, a cartridge system 1, a liquid container 2, and a manually driven pump 3. The central component of the cartridge system 1 is a cartridge 4 that is filled with a cement powder (not shown) for a bone cement. The cartridge system 1 is connected to the liquid container 2 and the pump 3 by means of a foot part 5. In this context, the foot part 5 forms, inter alia, the base of the compact vacuum mixing system.

The cartridge 4 has a cylindrical internal space with circular footprint. A cement powder is present in the internal space of the cartridge 4. Moreover, a mixing device 6 having two or more mixing vanes 6 that are fastened on a mixing tube 8 is arranged in the internal space of the cartridge 4. The mixing tube 8 is guided through a sterilisation plunger 9, such that it can be rotated and shifted in longitudinal direction. The sterilisation plunger 9 is located on the rear side of the cartridge 4, which arranged on top. For this purpose, the feed-through is designed to be pressure-tight and gas-tight. The sterilisation plunger 9 comprises a membrane (not shown) that is permeable for a sterilising gas, but impermeable for the cement powder. The sterilisation plunger 9 is inserted into the cartridge 4 after the cement powder is filled in and closes the internal space of the cartridge 4 with respect to the outside. Subsequently, the content of the cartridge 4 can be sterilised through the gas-permeable membrane using ethylene dioxide.

A sealing plunger 10 can be pushed into the sterilisation plunger 9 and can be connected to same in gas-tight and pressure-tight manner. The plungers 9, 10, which are fastened to each other, then together form a dispensing plunger 9, 10 by means of which the content of the cartridge 4 can be extruded through the floor-side opening. However, the sterilisation plunger 9 is initially locked on the opposite side (on the top in FIGS. 1, 3 and 5 to 7), whereby the locking can be detached.

A handle part 11 is attached on the mixing tube 8 outside the cartridge 4 by means of which the mixing vanes 6 on the inside of the cartridge 4, i.e. in the internal space of the cartridge 4, can be manually rotated and shifted in the longitudinal direction of the cartridge 4.

A feed-through that is connected to a connecting conduit 12 in the form of a flexible vacuum conduit 12 is provided in the sealing plunger 10. Apart from that, the sealing plunger 10 closes pressure-tight against the cartridge 4. The front side of the cartridge 4 (on the bottom in FIGS. 1, 3 and 5 to 7) is connected in pressure-tight manner to the liquid container 2 through the foot part 5 via a liquid conduit 14. A loop 16 in the form of siphon 16 is provided in the liquid conduit 14 and is used to prevent a monomer (not shown) contained in the liquid container 2 from inadvertently advancing into the cartridge 4.

The pump 3 comprises a stable hollow cylinder 20. An operating element 21 that can be pushed downward by hand is arranged on the top (on the top in FIGS. 1, 3 and 5 to 7) of the pump 3. The hollow cylinder 20 is subdivided into two parts in pressure tight manner by means of a plunger 22. For this purpose, the plunger 22 comprises a circumferential seal that closes off against the internal wall of the hollow cylinder 20. The plunger 22 and a rod 23 extending through a pressure-tight feed-through in a closure 24 are designed as a single part. The closure 24 closes off the hollow cylinder 20 on one side in pressure-tight manner. The vacuum conduit 12 is guided to the pump 3 such that the feed-through in the sealing plunger 10 is connected in pressure-tight manner to the pump 3, to the pumping space 26 of the pump 3 to be specific, via the vacuum conduit 12.

Figure 5:
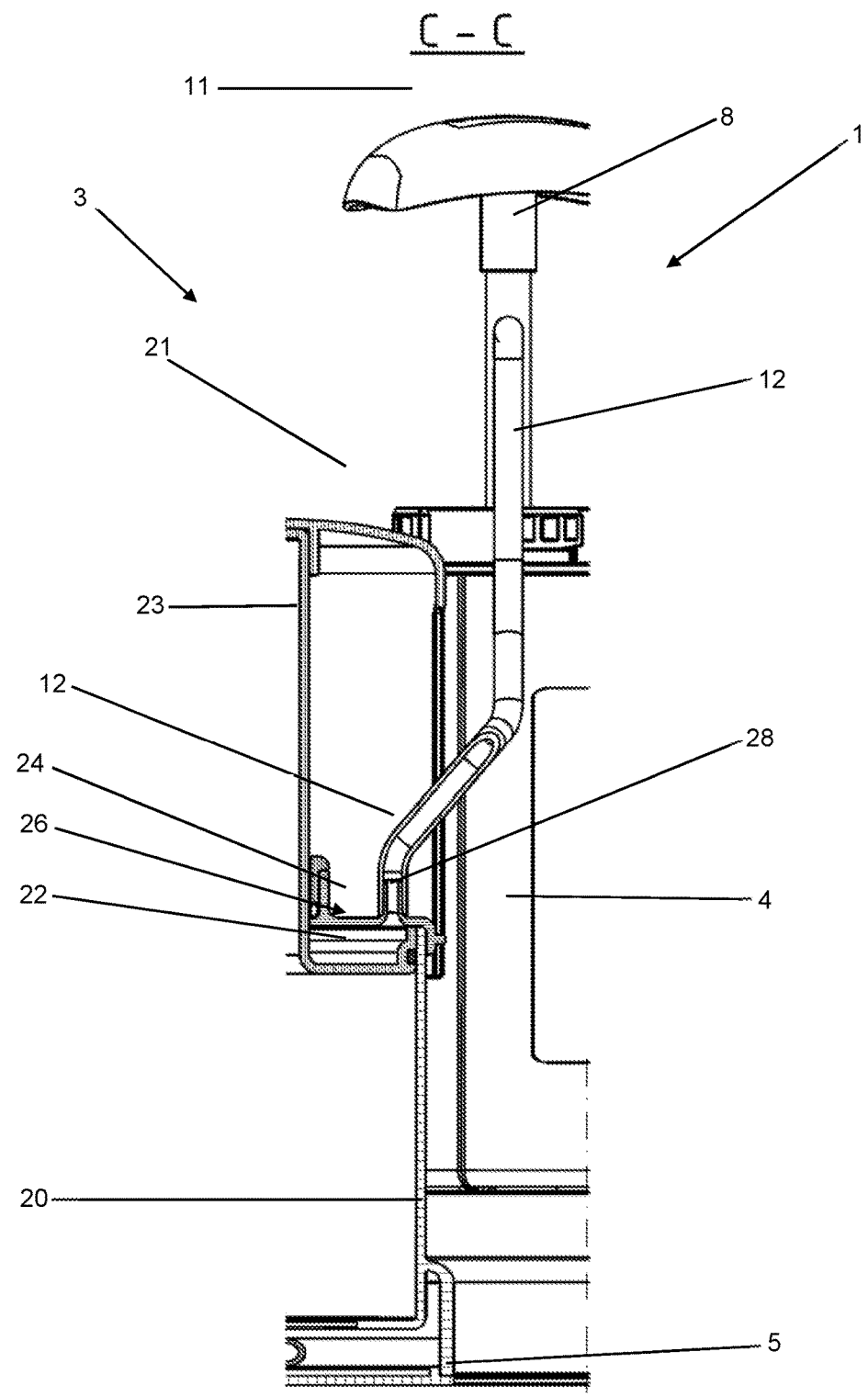
FIG. 5: shows a schematic cross-sectional view of a part of the vacuum mixing system according to FIGS. 1 to 4 sectioned along C-C according to FIG. 2.
Figure 6:
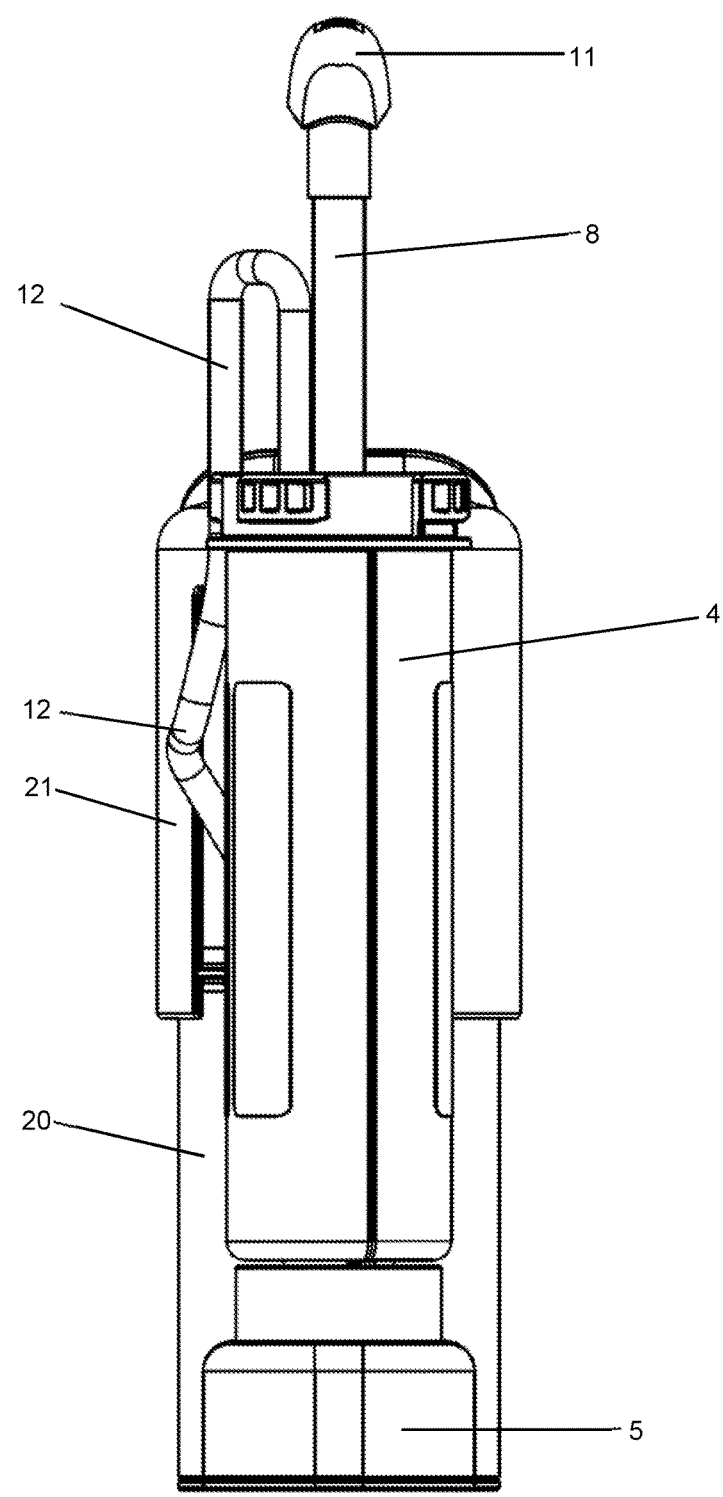
FIG. 6: shows a schematic lateral partial view of the vacuum mixing system according to FIGS. 1 to 5.

A mouth 28 opening into the vacuum conduit 12 and/or a connector 28 for the vacuum conduit 12 is provided in the closure 24 on the hollow cylinder 20 (shown in FIG. 5 only). The part of the internal space of the hollow cylinder 20 situated between the closure 24 and the plunger 22 forms the pumping space 26. A low pressure in the pumping space 26 can thus act through the vacuum conduit 12 up into the internal space of the cartridge 4 and/or a gas can be evacuated from the internal space the cartridge 4 when the sealing plunger 10 is connected to the sterilisation plunger 9 as shown in the figures, and the internal space of the cartridge 4 is thus sealed with respect to the outside except for the opening to the liquid conduit 14.

The cartridge 4 is fastened to the foot part 5 such as to be detachable in vertical direction. For this purpose, an opening having an internal thread is provided on the front side of the cartridge 4 that is screwed onto a socket 30, having an external thread, on the foot part 5. The liquid conduit 14 merges in the socket 30 through a powder-impermeable, but monomer liquid-permeable filter 32 into the internal space of the cartridge 4.

The liquid container 2 comprises a receptacle 39 for a glass ampoule 40. A glass ampoule 40 having a breakable head 42 is arranged in the liquid container 2. The glass ampoule 40 contains the monomer liquid. The receptacle 39 for the glass ampoule 40 is made of a flexible material such as, for example, rubber and can be bent manually in order to be able to manually break off the head 42 of the glass ampoule 40 inside the liquid container 2. The head 42 of the glass ampoule 40 can be broken off or sheared off by deforming the receptacle 39. For this purpose, the receptacle comprises a thicker section in the part of the neck between the head 42 and the body of the glass ampoule 40. Once the head 42 of the glass ampoule 40 is broken off, the monomer liquid flows from the glass ampoule 40. Fragments and shards of glass that may be generated as well as the broken-off ampoule head 42 are retained by a sieve 44 or filter 44 (see FIG. 7). In addition, a valve element (not shown) that can be opened by a rotating lever can also be provided at the inlet of the liquid container 2 into the liquid conduit 14.

The liquid container 2 is closed in by a lid 46 after the glass ampoule 40 has been inserted into the liquid container 2. To allow the monomer liquid to leak and/or flow out from the glass ampoule 40 without any problems, two passages 48 are provided in the lid 46 through which the air from outside can flow into the liquid container 2. After breaking the glass ampoule 40 open, the monomer liquid in the liquid container 2 is available and can be guided through the liquid conduit 14 into the internal space of the cartridge 4 by using a low pressure in the internal space of the cartridge 4 to aspirate the monomer liquid from the liquid container 2 into the internal space of the cartridge 4. This low pressure is generated by the pump 3. The monomer liquid can then be mixed with the cement powder in the internal space of the cartridge 4 by means of the mixing device 6 in a vacuum and/or at a low pressure in order to generate the bone cement and/or a bone cement paste.

According to the invention, the vacuum mixing system is characterised by the applicability of the following exemplary method according to the invention. The pump 3 is used by manually pushing and/or pressing the plunger 22 with the operating element 21 into the hollow cylinder 20. This is done once the cartridge 4 is made ready for use by inserting the sealing plunger 10, as is shown in the figures. In the process, the plunger 22 is moved in the direction of an opening in the floor of the hollow cylinder (on the bottom in FIGS. 3 and 7). This motion enlarges the pumping space 26. As a result, the pressure in the pumping space 26 is reduced. Gas flows from the vacuum conduit 12, the internal space of the cartridge 4, and the liquid conduit 14 into the pumping space 26. The internal space of the cartridge 4 is thus being evacuated.

Figure 1:
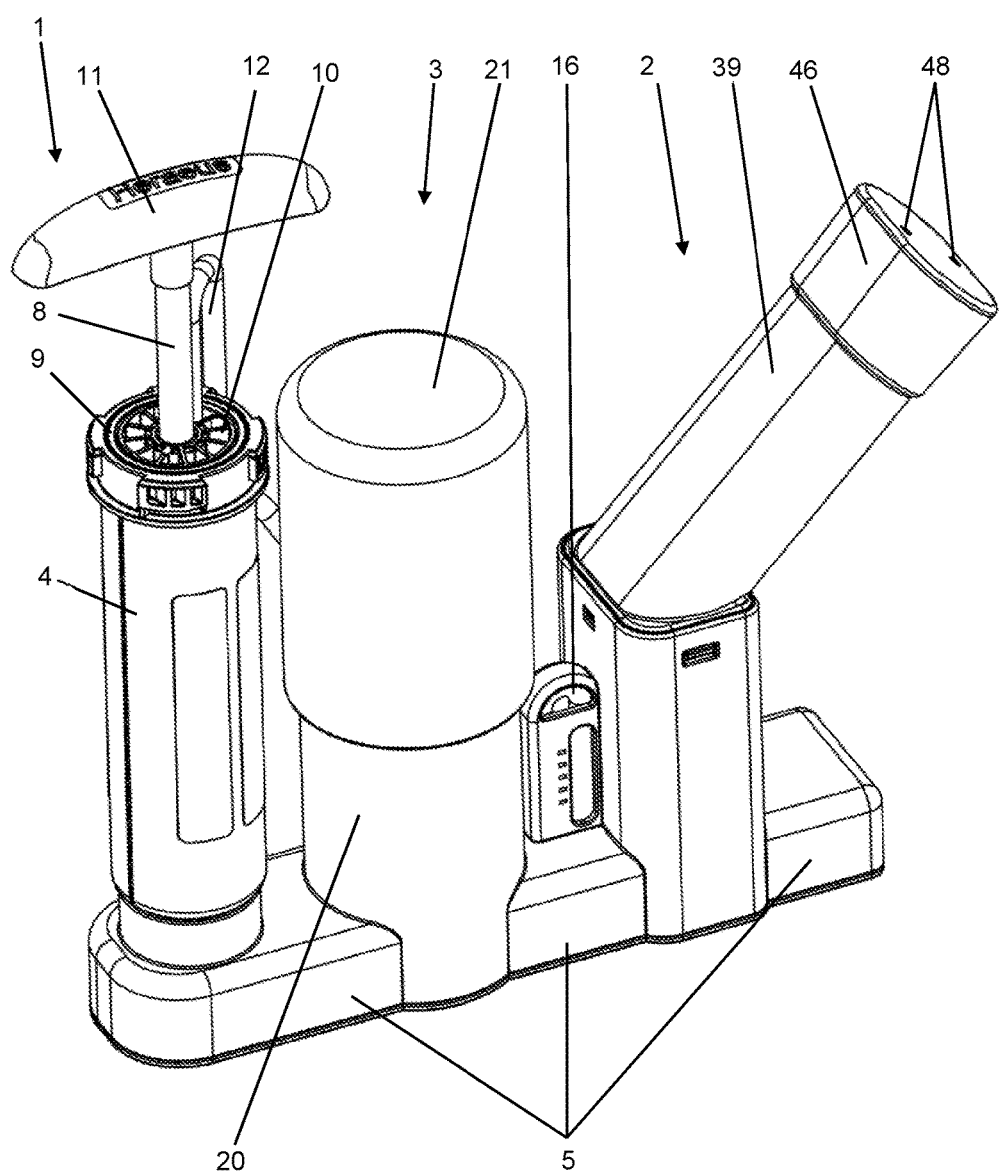
FIG. 1: shows a schematic perspective view of a vacuum mixing system according to the invention before the pumping process.
Figure 2:
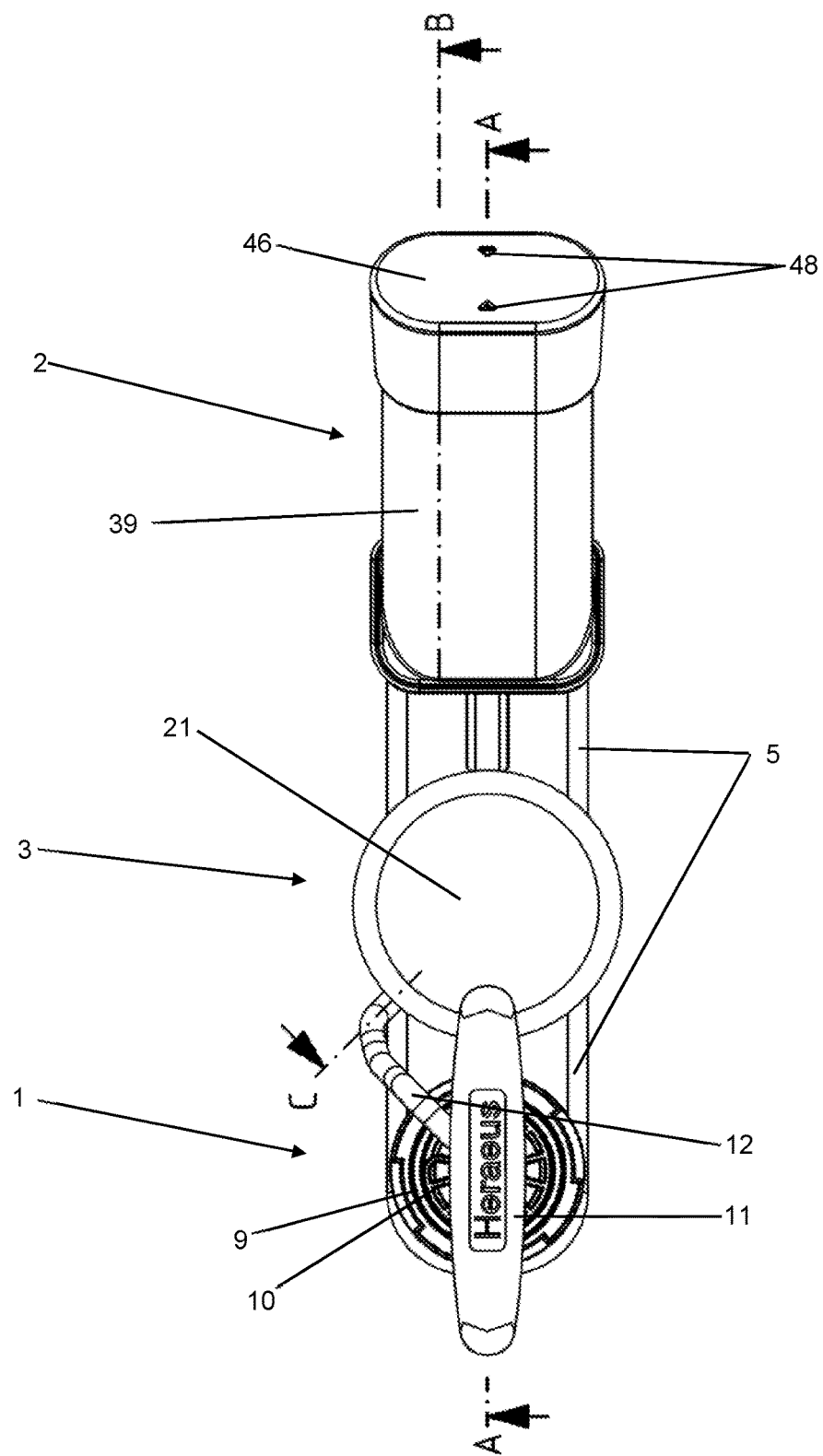
FIG. 2: shows a schematic top view of the vacuum mixing system according to FIG. 1 with three section planes A-A, B-B, and C-C.
Figure 3:
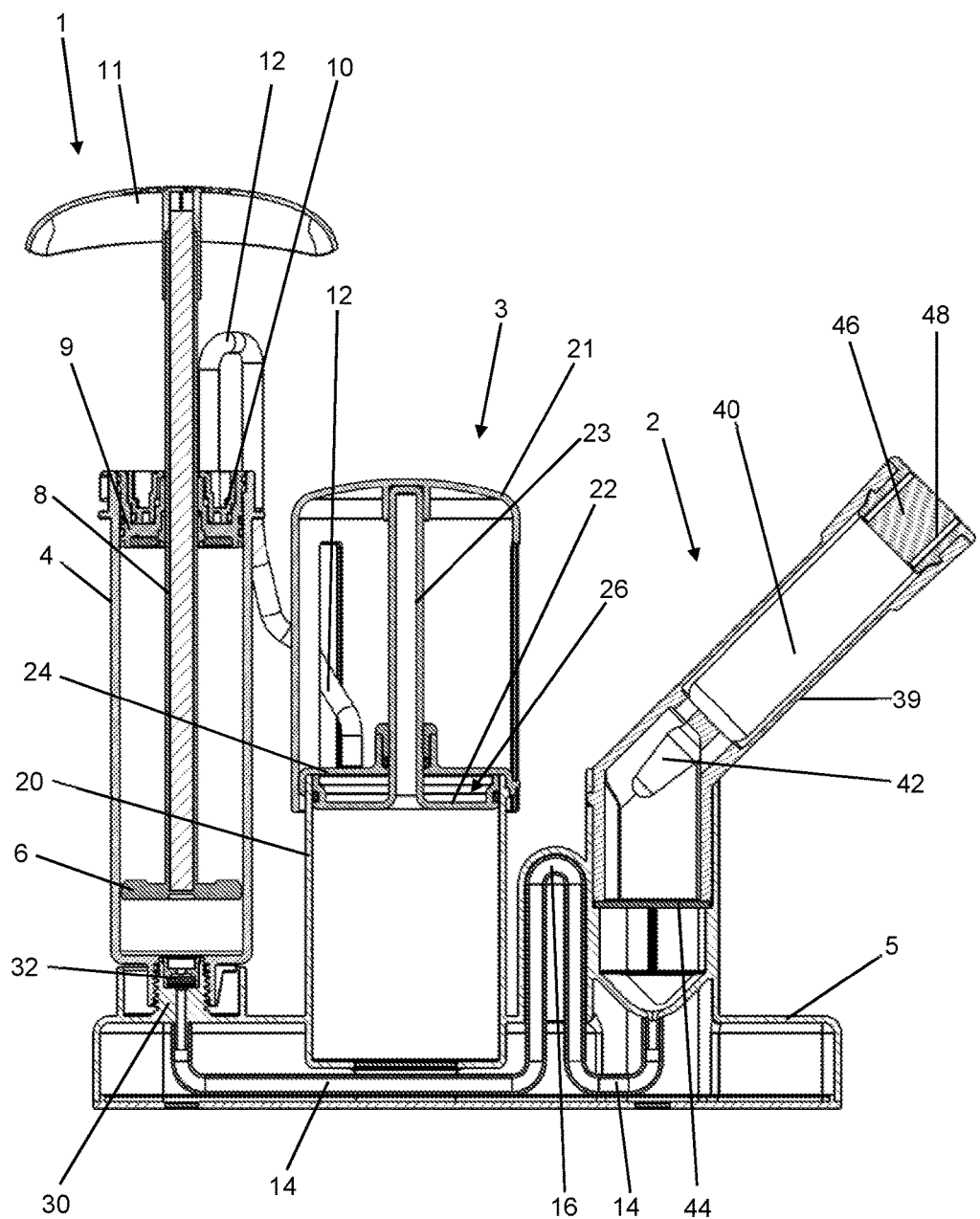
FIG. 3: shows a schematic cross-sectional view of the vacuum mixing system according to FIGS. 1 and 2 sectioned along A-A according to FIG. 2.
Figure 4:
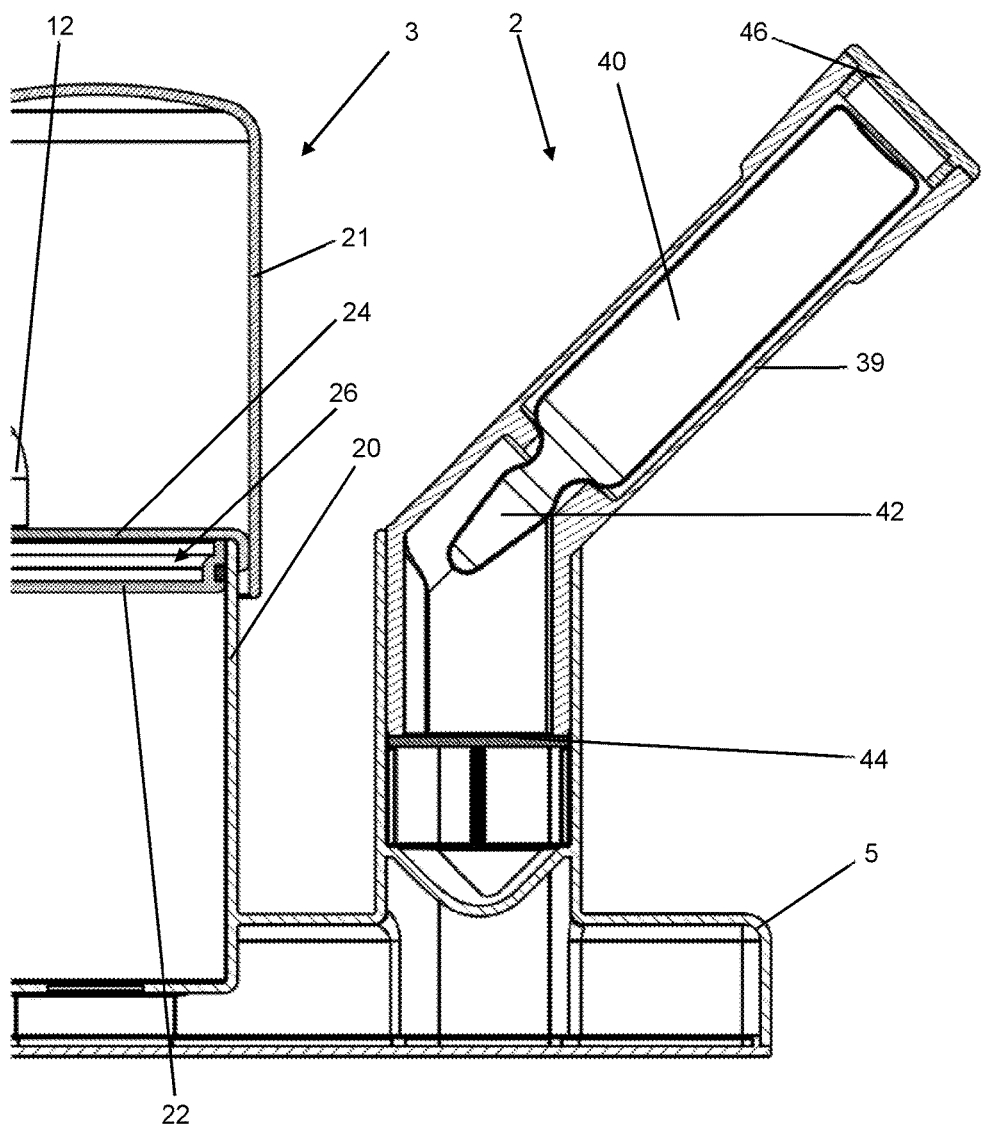
FIG. 4: shows a schematic cross-sectional view of a part of the vacuum mixing system according to FIGS. 1 to 3 sectioned along B-B according to FIG. 2.

The plunger 22 is moved to the end of the hollow cylinder 20 (on the bottom in FIGS. 3 and 7). This arrangement is shown in FIG. 7. The increase in the volume of the pumping space 26 must be sufficient to evacuate the gas from the vacuum conduit 12, the internal space of the cartridge 4, and the liquid conduit 14 and to draw the monomer liquid from the liquid container 2 into the internal space of the cartridge 4. For this purpose, the expanded pumping space 26, as shown in FIG. 3, is preferred to be larger than the volumes of the conduits 12, 14 of the internal space of the cartridge 4 and the liquid volume of the monomer liquid. It should be noted in this context that the figures show the size relationships of the pumping space 26 and other volumes only schematically.

Once the starting components have been mixed with the mixing vanes 6 in the internal space of the cartridge 4, the mixing tube 8 is pulled upwards out of the internal space of the cartridge 4 as far as it will go and can then be broken off at a predetermined breakage site. The sealing plunger 10 is rotated with respect to the sterilisation plunger 9 and thus the gas feed-through through the sealing plunger 10 is closed. The vacuum conduit 12 is then pulled off the sealing plunger 10. The cartridge 4 is unscrewed from the foot part 5 and a dispensing tube (not shown), by means of which the mixed bone cement can be applied, is screwed into the internal thread. The conveying plunger or dispensing plunger 9, 10 composed of the sterilisation plunger 9 and the sealing plunger 10 is unlocked and can be driven into the inside of the cartridge 4 by means of an application device (not shown). As a result, the content of the cartridge 4, i.e. the bone cement mixed at a low pressure, is extruded from the opposite opening and through the screwed-on dispensing tube arranged on the front side.

Except for the glass ampoule 40, the filter 32, and the starting components of the bone cement, the components of the vacuum mixing system can be manufactured from a plastic material by means of injection moulding. The conduits 12, 14 can consist of a different plastic material. The connecting conduit 12 must be flexible in order to be able to arrange the sealing plunger 10 in mobile manner on the mixing tube 8 and to enable a motion of the mouth 28 in the pumping space. A longitudinal cut is provided in the operating element 21 through which the connecting conduit 12 can glide when the operating element 21 and plunger 22 are moved.

The conduits 12, 14 are arranged in a housing made of plastics that forms the foot part 5, whereby the foot part 5 comprises a planar floor to allow the vacuum mixing system to be set up on a planar support.

Using the vacuum mixing system described above, the two starting components of the bone cement can be stored and mixed in a vacuum at any later point in time. The vacuum mixing system does not need to be connected to any external supply (power, water or compressed gas) in this context. There is no need for an internal energy store such as the battery or a tensioned spring to drive the vacuum mixing system. The energy required to generate the low pressure is also generated manually, just like the force required to open the glass ampoule 40.

The features of the invention disclosed in the preceding description and in the claims, figures, and exemplary embodiments, can be essential for the implementation of the various embodiments of the invention both alone and in any combination.

LIST OF REFERENCE NUMBERS

1 Cartridge system
2 Liquid container
3 Pump
4 Cartridge
5 Foot part
6 Mixing vanes
8 Mixing tube
9 Sterilisation plunger
10 Sealing plunger
11 Handle part
12 Connecting conduit/vacuum conduit
14 Liquid conduit
16 Loop/siphon
20 Hollow cylinder
21 Operating element
22 Plunger
23 Rod/tube
24 Closure
26 Pumping space
28 Mouth opening into the connecting conduit
30 Socket with external thread
32 Powder-impermeable and liquid-permeable filter
39 Receptacle for glass ampoule
40 Glass ampoule
42 Head of the glass ampoule
44 Sieve/filter
46 Lid
48 Ventilation passage

We claim:

1. A vacuum mixing system for mixing PMMA bone cement comprising:
at least one cartridge having an evacuable internal space for mixing of the bone cement and a front side,
a pump with a plunger movable by hand to generate a low pressure,
a container,
a liquid conduit connecting the container to the at least one cartridge,
and
a connecting conduit connecting the internal space of the at least one cartridge to the pump,
wherein the pump comprises an operating element operable from outside and connected appropriately to the plunger such that it is suitable for moving the plunger in the pump by hand such that a low pressure can be generated such that the low pressure of the pump is usable to evacuate gas from the internal space of the at least one cartridge through the connecting conduit,
wherein a cement powder is contained in the cartridge and the container contains a monomer liquid, wherein the container is connected via the liquid conduit to the cartridge, whereby the liquid conduit connects at the front side of the cartridge, and the liquid conduit forms a pressure tight connection to the container.

2. The vacuum mixing system according to claim 1, wherein the pump comprises a gas-tight pumping space on the inside and has the plunger movable by hand limiting the pumping space is arranged inside the pump, wherein the plunger is drivable by hand in an unidirectionally, such that the motion of the plunger enlarges the pumping space and the low pressure thus arising in the pumping space allows the internal space of the at least one cartridge to be evacuated through the connecting conduit.

3. The vacuum mixing system according to claim 2, wherein the volume enlargement of the pumping space is at least equal to the free volume of the internal space of the cartridge.

4. The vacuum mixing system according to claim 1, wherein the vacuum mixing system comprises a mixing device for the mixing of the content of the at least one cartridge, wherein the mixing device is arranged in the internal space of the cartridge and/or can be driven manually or through a motor.

5. The vacuum mixing system according to claim 1, wherein the plunger is supported in a hollow cylinder such as to be axially mobile, wherein the hollow cylinder is closed on a first side or is closed except for one feed-through for a rod connected to an operating element and the plunger, wherein a pumping space is formed in the hollow cylinder between the plunger and the first closed side.

6. The vacuum mixing system according to claim 1, wherein the plunger is connected to the operating element by means of a rod and the plunger is movable in the pump by pushing the operating element.

7. The vacuum mixing system according to claim 1, wherein a mobile dispensing plunger for dispensing the mixed bone cement from the cartridge is arranged in the internal space of the cartridge, wherein the dispensing plunger is or can be locked in place in detachable manner in order to prevent the dispensing plunger from moving in response to the effect of the low pressure.

8. The vacuum mixing system according to claim 7, wherein the dispensing plunger comprises a passage with a gas-permeable pore disk that is impermeable for the cement powder, wherein the passage with the pore disk connects the internal space of the cartridge to the surroundings in gas-permeable manner, wherein the passage can be closed in gas-tight manner by means of a sealing plunger of the dispensing plunger.

9. The vacuum mixing system according to claim 1, wherein the cartridge is a cement cartridge filled with the cement powder, wherein the container is connected, in liquid-impermeable manner, to the internal space of the cement cartridge through a separating element that can be opened, and/or the internal space of the cement cartridge is or can be connected to the pump (3) in gas-so manner.

10. The vacuum mixing system according to claim 1, wherein the cartridge, the pump, the separate container, and all connecting conduits are connected to a common foot part either affixed and/or in detachable manner, wherein the pump, the separate container, and all connecting conduits affixed to the foot part and the cartridge be connected to the foot part in detachable manner.

11. The vacuum mixing system according to claim 1, wherein the liquid conduit, which is provided between the separate container and the internal space of the cartridge, comprises an upward facing loop, wherein an apex of the loop is situated above a junction under a monomer container that is arranged in the separate container.

12. The vacuum mixing system according to claim 1, wherein the pump comprises:
- a hollow cylinder, wherein the hollow cylinder is or can be connected to the internal space of the cartridge;
- a gas-tight closure on one end of the hollow cylinder;
- a plunger that is arranged in the hollow cylinder such as to be gas-tight and axially mobile; and
- at least one operating element that can be operated by hand and can be used to move the plunger in the pump by hand,
- wherein the plunger can be moved axially in opposite direction with respect to the closure when the plunger is moved by the at least one operating element that can be operated by hand and thus evacuates the gas from the internal space of the cartridge.

13. A method for the mixing of polymethylmethacrylate bone cement in an internal space of the cartridge of a vacuum mixing system according to claim 1, the method comprising
- moving the manually driven plunger of a pump of the vacuum mixing system to generate a low pressure in the pump, wherein the pump driven is used to evacuate the internal space of the cartridge from above, wherein a cement powder is contained in the internal space of the cartridge and a gas is evacuated from the internal space of the cartridge by the pump, wherein a monomer liquid is introduced into the internal space of the cartridge from below by the low pressure and then the monomer liquid and the cement powder is mixed in the evacuated internal space of the cartridge to form a bone cement.

14. The method according to claim 13, wherein a volume of a pumping space of the pump is enlarged by manually moving the plunger and in that the internal space of the cartridge is evacuated by the low pressure thus generated.

15. The method according to claim 13, wherein the monomer liquid is aspirated into the internal space of the cartridge by the low pressure in the pump.

16. The method according to claim 13, wherein the plunger of the pump is moved by hand, wherein a low pressure with respect to the ambient atmosphere is generated in the pump;
- wherein gas is aspirated from the internal space of the cartridge from above through a connecting conduit into the hollow cylinder and the monomer liquid is aspirated from below into the cartridge and into the cement powder;
- followed by the cement powder being mixed, manually or motor-driven, with the monomer liquid by means of a mixing device;
- followed by the cartridge with the mixed cement dough being removed; and
- the cement dough being extruded from the cartridge by moving a dispensing plunger axially.

17. The method according to claim 13, wherein
- the monomer liquid is arranged in a container that is separate from the cartridge, wherein the monomer liquid is contained in a glass ampoule;
- the glass ampoule is opened before the plunger is moved by hand such that a liquid-permeable connection is established between the internal space of the cartridge and the container;
- followed by the plunger being moved axially in the hollow cylinder, wherein a low pressure with respect to the ambient atmosphere is generated;
- wherein gas is aspirated from the internal space of the cartridge through the connecting conduit into the hollow cylinder, and monomer liquid is aspirated into the cartridge through the low pressure formed in the internal space of the cartridge.

* * * * *